(12) United States Patent
Glass et al.

(10) Patent No.: US 7,754,207 B2
(45) Date of Patent: Jul. 13, 2010

(54) METHODS OF TREATING PULMONARY FIBROSIS

(75) Inventors: William Glass, Radnor, PA (US); Lynne Murray, Malvern, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 134 days.

(21) Appl. No.: 11/925,330

(22) Filed: Oct. 26, 2007

(65) Prior Publication Data

US 2008/0311128 A1 Dec. 18, 2008

Related U.S. Application Data

(60) Provisional application No. 60/863,237, filed on Oct. 27, 2006.

(51) Int. Cl.
*A61K 39/395* (2006.01)
*C07K 14/435* (2006.01)

(52) U.S. Cl. .................................. 424/130.1; 530/351
(58) Field of Classification Search ....................... None
See application file for complete search history.

(56) References Cited

U.S. PATENT DOCUMENTS

| 5,514,555 | A | 5/1996 | Springer et al. |
| 5,766,866 | A | 6/1998 | Center et al. |
| 5,807,549 | A | 9/1998 | Center et al. |
| 5,807,712 | A | 9/1998 | Center et al. |
| 5,919,700 | A | 7/1999 | Borden et al. |
| 5,985,613 | A | 11/1999 | Kurth et al. |
| 6,338,844 | B1 | 1/2002 | Kurth et al. |
| 6,444,202 | B1 | 9/2002 | Kurth et al. |
| 6,506,582 | B1 | 1/2003 | Kurth et al. |
| 6,723,697 | B2 | 4/2004 | Center et al. |
| 2002/0147151 | A1 | 10/2002 | Center et al. |
| 2003/0021780 | A1 | 1/2003 | Smith et al. |
| 2003/0022911 | A1 | 1/2003 | Smith et al. |

OTHER PUBLICATIONS

Glass et al., Generation of bleomycin-induced lung fibrosis is independent of IL-16. Cytokine 6 (1):17-23, 2009.*
Mathy, et al., "Cutting Edge: CD4 Is Not Required for the Functional Activity of IL-16," The Journal of Immunology, 164: 4429-4432 (2000).
Cruikshank, et al., "Interleukin-16," Journal of Leukocyte Biology, 67: 757-766 (2000).
Zhang, et al., "Processing and Activation of Pro-Interleukin-16 by Caspase-3," The Journal of Biological Chemistry, 273(20): 1144-1149 (1998).
Reich, et al., "Evidence for a role of Langerhans cell-derived IL-16 in atopic dermatitis," Journal of Allergy and Clinical Immunology, 109: 681-687 (2002).
Lard, et al., Enhanced Concentration of Interleukin 16 Are Associated with Joint Destruction in Patients with Rheumatoid Arthritis, Journal of Rheumatology, 31: 35-39 (2004).
Krug, et al., "Interleukin 16 and T-cell Chemoattractant Activity in Bronchoalveolar Lavage 24 Hours after Allergen Challenge in Asthma," American Journal of Respiratory and Critical Care Medicine, 162: 105-111 (2000).

* cited by examiner

*Primary Examiner*—Ruixiang Li
(74) *Attorney, Agent, or Firm*—Eric Dichter

(57) ABSTRACT

Methods for treating pathological pulmonary conditions and bleomycin associated pulmonary fibrosis administer IL-16 antagonists, for example, anti-IL-16 antibodies, to subjects.

4 Claims, 5 Drawing Sheets

SEQUENCE LISTING

<160> NUMBER OF SEQ ID NOS: 5

<210> SEQ ID NO 1
<211> LENGTH: 631
<212> TYPE: PRT
<213> ORGANISM: Homo sapiens

```
<400> SEQUENCE: 1

Met Asp Tyr Ser Phe Asp Thr Thr Ala Glu Asp Pro Trp Val Arg Ile
 1               5                  10                  15

Ser Asp Cys Ile Lys Asn Leu Phe Ser Pro Ile Met Ser Glu Asn His
            20                  25                  30

Gly His Met Pro Leu Gln Pro Asn Ala Ser Leu Asn Glu Glu Glu Gly
        35                  40                  45

Thr Gln Gly His Pro Asp Gly Thr Pro Pro Lys Leu Asp Thr Ala Asn
    50                  55                  60

Gly Thr Pro Lys Val Tyr Lys Ser Ala Asp Ser Ser Thr Val Lys Lys
65                  70                  75                  80

Gly Pro Pro Val Ala Pro Lys Pro Ala Trp Phe Arg Gln Ser Leu Lys
                85                  90                  95

Gly Leu Arg Asn Arg Ala Ser Asp Pro Arg Gly Leu Pro Asp Pro Ala
            100                 105                 110

Leu Ser Thr Gln Pro Ala Pro Ala Ser Arg Glu His Leu Gly Ser His
        115                 120                 125

Ile Arg Ala Ser Ser Ser Ser Ser Ile Arg Gln Arg Ile Ser Ser
    130                 135                 140

Phe Glu Thr Phe Gly Ser Ser Gln Leu Pro Asp Lys Gly Ala Gln Arg
145                 150                 155                 160

Leu Ser Leu Gln Pro Ser Ser Gly Glu Ala Ala Lys Pro Leu Gly Lys
                165                 170                 175

His Glu Glu Gly Arg Phe Ser Gly Leu Leu Gly Arg Gly Ala Ala Pro
            180                 185                 190

Thr Leu Val Pro Gln Gln Pro Glu Gln Val Leu Ser Ser Gly Ser Pro
        195                 200                 205

Ala Ala Ser Glu Ala Arg Asp Pro Gly Val Ser Glu Ser Pro Pro
    210                 215                 220

Gly Arg Gln Pro Asn Gln Lys Thr Leu Pro Pro Gly Pro Asp Pro Leu
225                 230                 235                 240

Leu Arg Leu Leu Ser Thr Gln Ala Glu Glu Ser Gln Gly Pro Val Leu
                245                 250                 255

Lys Met Pro Ser Gln Arg Ala Arg Ser Phe Pro Leu Thr Arg Ser Gln
            260                 265                 270

Ser Cys Glu Thr Lys Leu Leu Asp Glu Lys Thr Ser Lys Leu Tyr Ser
        275                 280                 285

Ile Ser Ser Gln Val Ser Ala Val Met Lys Ser Leu Leu Cys Leu
    290                 295                 300

Pro Ser Ser Ile Ser Cys Ala Gln Thr Pro Cys Ile Pro Lys Glu Gly
305                 310                 315                 320

Ala Ser Pro Thr Ser Ser Asn Glu Asp Ser Ala Ala Asn Gly Ser
                325                 330                 335

Ala Glu Thr Ser Ala Leu Asp Thr Gly Phe Ser Leu Asn Leu Ser Glu
            340                 345                 350

Leu Arg Glu Tyr Thr Glu Gly Leu Thr Glu Ala Lys Glu Asp Asp
        355                 360                 365

Gly Asp His Ser Ser Leu Gln Ser Gly Gln Ser Val Ile Ser Leu Leu
    370                 375                 380

Ser Ser Glu Glu Leu Lys Lys Leu Ile Glu Glu Val Lys Val Leu Asp
385                 390                 395                 400

Glu Ala Thr Leu Lys Gln Leu Asp Gly Ile His Val Thr Ile Leu His
                405                 410                 415
```

```
Lys Glu Glu Gly Ala Gly Leu Gly Phe Ser Leu Ala Gly Gly Ala Asp
            420                 425                 430
Leu Glu Asn Lys Val Ile Thr Val His Arg Val Phe Pro Asn Gly Leu
        435                 440                 445
Ala Ser Gln Glu Gly Thr Ile Gln Lys Gly Asn Glu Val Leu Ser Ile
    450                 455                 460
Asn Gly Lys Ser Leu Lys Gly Thr Thr His His Asp Ala Leu Ala Ile
465                 470                 475                 480
Leu Arg Gln Ala Arg Glu Pro Arg Gln Ala Val Ile Val Thr Arg Lys
                485                 490                 495
Leu Thr Pro Glu Ala Met Pro Asp Leu Asn Ser Ser Thr Asp Ser Ala
            500                 505                 510
Ala Ser Ala Ser Ala Ala Ser Asp Val Ser Val Glu Ser Thr Ala Glu
        515                 520                 525
Ala Thr Val Cys Thr Val Thr Leu Glu Lys Met Ser Ala Gly Leu Gly
    530                 535                 540
Phe Ser Leu Glu Gly Gly Lys Gly Ser Leu His Gly Asp Lys Pro Leu
545                 550                 555                 560
Thr Ile Asn Arg Ile Phe Lys Gly Ala Ala Ser Glu Gln Ser Glu Thr
                565                 570                 575
Val Gln Pro Gly Asp Glu Ile Leu Gln Leu Gly Gly Thr Ala Met Gln
            580                 585                 590
Gly Leu Thr Arg Phe Glu Ala Trp Asn Ile Ile Lys Ala Leu Pro Asp
        595                 600                 605
Gly Pro Val Thr Ile Val Ile Arg Arg Lys Ser Leu Gln Ser Lys Glu
    610                 615                 620
Thr Thr Ala Ala Gly Asp Ser
625                 630

<210> SEQ ID NO 2
<211> LENGTH: 121
<212> TYPE: PRT
<213> ORGANISM: Homo sapiens

<400> SEQUENCE: 2

Ser Ala Ala Ser Ala Ser Ala Ala Ser Asp Val Ser Val Glu Ser Thr
1               5                   10                  15
Ala Glu Ala Thr Val Cys Thr Val Thr Leu Glu Lys Met Ser Ala Gly
            20                  25                  30
Leu Gly Phe Ser Leu Glu Gly Gly Lys Gly Ser Leu His Gly Asp Lys
        35                  40                  45
Pro Leu Thr Ile Asn Arg Ile Phe Lys Gly Ala Ala Ser Glu Gln Ser
    50                  55                  60
Glu Thr Val Gln Pro Gly Asp Glu Ile Leu Gln Leu Gly Gly Thr Ala
65                  70                  75                  80
Met Gln Gly Leu Thr Arg Phe Glu Ala Trp Asn Ile Ile Lys Ala Leu
                85                  90                  95
Pro Asp Gly Pro Val Thr Ile Val Ile Arg Arg Lys Ser Leu Gln Ser
            100                 105                 110
Lys Glu Thr Thr Ala Ala Gly Asp Ser
        115                 120

<210> SEQ ID NO 3
<211> LENGTH: 846
<212> TYPE: PRT
```

<213> ORGANISM: Homo sapiens

<400> SEQUENCE: 3

```
Ser Leu Trp Gly Leu Val Ser Lys Met Pro Pro Glu Lys Val Gln Arg
 1               5                  10                  15

Leu Tyr Val Asp Phe Pro Gln His Leu Arg His Leu Leu Gly Asp Trp
            20                  25                  30

Leu Glu Ser Gln Pro Trp Glu Phe Leu Val Gly Ser Asp Ala Phe Cys
        35                  40                  45

Cys Asn Leu Ala Ser Ala Leu Leu Ser Asp Thr Val Gln His Leu Gln
    50                  55                  60

Ala Ser Val Gly Glu Gln Gly Glu Gly Ser Thr Ile Leu Gln His Ile
65                  70                  75                  80

Ser Thr Leu Glu Ser Ile Tyr Gln Arg Asp Pro Leu Lys Leu Val Ala
                85                  90                  95

Thr Phe Arg Gln Ile Leu Gln Gly Glu Lys Lys Ala Val Met Glu Gln
            100                 105                 110

Phe Arg His Leu Pro Met Pro Phe His Trp Lys Gln Glu Glu Leu Lys
        115                 120                 125

Phe Lys Thr Gly Leu Arg Arg Leu Gln His Arg Val Gly Glu Ile His
    130                 135                 140

Leu Leu Arg Glu Ala Leu Gln Lys Gly Ala Glu Ala Gly Gln Val Ser
145                 150                 155                 160

Leu His Ser Leu Ile Glu Thr Pro Ala Asn Gly Thr Gly Pro Ser Glu
                165                 170                 175

Ala Leu Ala Met Leu Leu Gln Glu Thr Thr Gly Glu Leu Glu Ala Ala
            180                 185                 190

Lys Ala Leu Val Leu Lys Arg Ile Gln Ile Trp Lys Arg Gln Gln Gln
        195                 200                 205

Leu Ala Gly Asn Gly Ala Pro Phe Glu Glu Ser Leu Ala Pro Leu Gln
    210                 215                 220

Glu Arg Cys Glu Ser Leu Val Asp Ile Tyr Ser Gln Leu Gln Gln Glu
225                 230                 235                 240

Val Gly Ala Ala Gly Gly Glu Leu Glu Pro Lys Thr Arg Ala Ser Leu
                245                 250                 255

Thr Gly Arg Leu Asp Glu Val Leu Arg Thr Leu Val Thr Ser Cys Phe
            260                 265                 270

Leu Val Glu Lys Gln Pro Pro Gln Val Leu Lys Thr Gln Thr Lys Phe
        275                 280                 285

Gln Ala Gly Val Arg Phe Leu Leu Gly Leu Arg Phe Leu Gly Ala Pro
    290                 295                 300

Ala Lys Pro Pro Leu Val Arg Ala Asp Met Val Thr Glu Lys Gln Ala
305                 310                 315                 320

Arg Glu Leu Ser Val Pro Gln Gly Pro Gly Ala Gly Ala Glu Ser Thr
                325                 330                 335

Gly Glu Ile Ile Asn Asn Thr Val Pro Leu Glu Asn Ser Ile Pro Gly
            340                 345                 350

Asn Cys Cys Ser Ala Leu Phe Lys Asn Leu Leu Leu Lys Lys Ile Lys
        355                 360                 365

Arg Cys Glu Arg Lys Gly Thr Glu Ser Val Thr Glu Glu Lys Cys Ala
    370                 375                 380

Val Leu Phe Ser Ala Ser Phe Thr Leu Gly Pro Gly Lys Leu Pro Ile
385                 390                 395                 400
```

-continued

```
Gln Leu Gln Ala Leu Ser Leu Pro Leu Val Ile Val His Gly Asn
            405                 410                 415

Gln Asp Asn Asn Ala Lys Ala Thr Ile Leu Trp Asp Asn Ala Phe Ser
            420                 425                 430

Glu Met Asp Arg Val Pro Phe Val Val Ala Glu Arg Val Pro Trp Glu
            435                 440                 445

Lys Met Cys Glu Thr Leu Asn Leu Lys Phe Met Ala Glu Val Gly Thr
450                 455                 460

Asn Arg Gly Leu Leu Pro Glu His Phe Leu Phe Leu Ala Gln Lys Ile
465                 470                 475                 480

Phe Asn Asp Asn Ser Leu Ser Met Glu Ala Phe Gln His Arg Ser Val
            485                 490                 495

Ser Trp Ser Gln Phe Asn Lys Glu Ile Leu Leu Gly Arg Gly Phe Thr
            500                 505                 510

Phe Trp Gln Trp Phe Asp Gly Val Leu Asp Leu Thr Lys Arg Cys Leu
            515                 520                 525

Arg Ser Tyr Trp Ser Asp Arg Leu Ile Ile Gly Phe Ile Ser Lys Gln
            530                 535                 540

Tyr Val Thr Ser Leu Leu Leu Asn Glu Pro Asp Gly Thr Phe Leu Leu
545                 550                 555                 560

Arg Phe Ser Asp Ser Glu Ile Gly Gly Ile Thr Ile Ala His Val Ile
            565                 570                 575

Arg Gly Gln Asp Gly Ser Pro Gln Ile Glu Asn Ile Gln Pro Phe Ser
            580                 585                 590

Ala Lys Asp Leu Ser Ile Arg Ser Leu Gly Asp Arg Ile Arg Asp Leu
            595                 600                 605

Ala Gln Leu Lys Asn Leu Tyr Pro Lys Lys Pro Lys Asp Glu Ala Phe
610                 615                 620

Arg Ser His Tyr Lys Pro Glu Gln Met Gly Lys Asp Gly Arg Gly Tyr
625                 630                 635                 640

Val Pro Ala Thr Ile Lys Met Thr Val Glu Arg Asp Gln Pro Leu Pro
            645                 650                 655

Thr Pro Glu Leu Gln Met Pro Thr Met Val Pro Ser Tyr Asp Leu Gly
            660                 665                 670

Met Ala Pro Asp Ser Ser Met Ser Met Gln Leu Gly Pro Asp Met Val
            675                 680                 685

Pro Gln Val Tyr Pro Pro His Ser His Ser Ile Pro Pro Tyr Gln Gly
            690                 695                 700

Leu Ser Pro Glu Glu Ser Val Asn Val Leu Ser Ala Phe Gln Glu Pro
705                 710                 715                 720

His Leu Gln Met Pro Pro Ser Leu Gly Gln Met Ser Leu Pro Phe Asp
            725                 730                 735

Gln Pro His Pro Gln Gly Leu Leu Pro Cys Gln Pro Gln Glu His Ala
            740                 745                 750

Val Ser Ser Pro Asp Pro Leu Leu Cys Ser Asp Val Thr Met Val Glu
            755                 760                 765

Asp Ser Cys Leu Ser Gln Pro Val Thr Ala Phe Pro Gln Gly Thr Trp
            770                 775                 780

Ile Gly Glu Asp Ile Phe Pro Pro Leu Leu Pro Pro Thr Glu Gln Asp
785                 790                 795                 800

Leu Thr Lys Leu Leu Leu Glu Gly Gln Gly Glu Ser Gly Gly Gly Ser
            805                 810                 815

Leu Gly Ala Gln Pro Leu Leu Gln Pro Ser His Tyr Gly Gln Ser Gly
```

```
                   820                 825                 830
Ile Ser Met Ser His Met Asp Leu Arg Ala Asn Pro Ser Trp
        835                 840                 845

<210> SEQ ID NO 4
<211> LENGTH: 624
<212> TYPE: PRT
<213> ORGANISM: Mus musculus

<400> SEQUENCE: 4

Met Asp Tyr Ser Phe Asp Ile Thr Ala Glu Asp Pro Trp Val Arg Ile
 1               5                  10                  15

Ser Asp Cys Ile Lys Asn Leu Phe Ser Pro Ile Met Ser Glu Asn His
            20                  25                  30

Ser His Thr Pro Leu Gln Pro Asn Thr Ser Leu Gly Glu Glu Asp Gly
        35                  40                  45

Thr Gln Gly Cys Pro Glu Gly Gly Leu Ser Lys Met Asp Ala Ala Asn
    50                  55                  60

Gly Ala Pro Arg Val Tyr Lys Ser Ala Asp Gly Ser Thr Val Lys Lys
65                  70                  75                  80

Gly Pro Pro Val Ala Pro Lys Pro Ala Trp Phe Arg Gln Ser Leu Lys
                85                  90                  95

Gly Leu Arg Asn Arg Ala Pro Asp Pro Arg Arg Pro Pro Glu Val Ala
            100                 105                 110

Ser Ala Ile Gln Pro Thr Pro Val Ser Arg Asp Pro Gly Pro Gln
        115                 120                 125

Pro Gln Ala Ser Ser Ser Ile Arg Gln Arg Ile Ser Ser Phe Glu Asn
    130                 135                 140

Phe Gly Ser Ser Gln Leu Pro Asp Arg Gly Val Gln Arg Leu Ser Leu
145                 150                 155                 160

Gln Pro Ser Ser Gly Glu Thr Thr Lys Phe Pro Gly Lys Gln Asp Gly
                165                 170                 175

Gly Arg Phe Ser Gly Leu Leu Gly Gln Gly Ala Thr Val Thr Ala Lys
            180                 185                 190

His Arg Gln Thr Glu Val Glu Ser Met Ser Thr Thr Phe Pro Asn Ser
        195                 200                 205

Ser Glu Val Arg Asp Pro Gly Leu Pro Glu Ser Pro Pro Ser Gln
    210                 215                 220

Arg Pro Ser Thr Lys Ala Leu Ser Pro Asp Pro Leu Leu Arg Leu Leu
225                 230                 235                 240

Thr Thr Gln Ser Glu Asp Thr Gln Gly Pro Gly Leu Lys Met Pro Ser
                245                 250                 255

Gln Arg Ala Arg Ser Phe Pro Leu Thr Arg Thr Gln Ser Cys Glu Thr
            260                 265                 270

Lys Leu Leu Asp Glu Lys Ala Ser Lys Leu Tyr Ser Ile Ser Ser Gln
        275                 280                 285

Leu Ser Ser Ala Val Met Lys Ser Leu Leu Cys Leu Pro Ser Ser Val
    290                 295                 300

Ser Cys Gly Gln Ile Thr Cys Ile Pro Lys Glu Arg Val Ser Pro Lys
305                 310                 315                 320

Ser Pro Cys Asn Asn Ser Ala Ala Glu Gly Phe Gly Glu Ala Met
                325                 330                 335

Ala Ser Asp Thr Gly Phe Ser Leu Asn Leu Ser Glu Leu Arg Glu Tyr
            340                 345                 350
```

Ser Glu Gly Leu Thr Glu Pro Gly Glu Thr Glu Asp Arg Asn His Cys
            355                 360                 365

Pro Ser Gln Ala Gly Gln Ser Val Ile Ser Leu Ser Ala Glu Glu
        370                 375                 380

Leu Glu Lys Leu Ile Glu Val Arg Val Leu Asp Glu Ala Thr Leu
385                 390                 395                 400

Lys Gln Leu Asp Ser Ile His Val Thr Ile Leu His Lys Glu Gly
                405                 410                 415

Ala Gly Leu Gly Phe Ser Leu Ala Gly Gly Ala Asp Leu Glu Asn Lys
            420                 425                 430

Val Ile Thr Val His Arg Val Phe Pro Asn Gly Leu Ala Ser Gln Glu
            435                 440                 445

Gly Thr Ile Gln Lys Gly Asn Glu Val Leu Ser Ile Asn Gly Lys Ser
            450                 455                 460

Leu Lys Gly Ala Thr His Asn Asp Ala Leu Ala Ile Leu Arg Gln Ala
465                 470                 475                 480

Arg Asp Pro Arg Gln Ala Val Ile Val Thr Arg Arg Thr Thr Val Glu
                485                 490                 495

Ala Thr His Asp Leu Asn Ser Ser Thr Asp Ser Ala Ala Ser Ala Ser
            500                 505                 510

Ala Ala Ser Asp Ile Ser Val Glu Ser Lys Glu Ala Thr Ala Cys Thr
            515                 520                 525

Val Thr Leu Glu Lys Thr Ser Ala Gly Leu Gly Phe Ser Leu Glu Gly
            530                 535                 540

Gly Lys Gly Ser Leu His Gly Asp Lys Pro Leu Thr Ile Asn Arg Ile
545                 550                 555                 560

Phe Lys Gly Thr Glu Gln Gly Glu Met Val Gln Pro Gly Asp Glu Ile
                565                 570                 575

Leu Gln Leu Ala Gly Thr Ala Val Gln Gly Leu Thr Arg Phe Glu Ala
            580                 585                 590

Trp Asn Val Ile Lys Ala Leu Pro Asp Gly Pro Val Thr Ile Val Ile
            595                 600                 605

Arg Arg Thr Ser Leu Gln Cys Lys Gln Thr Thr Ala Ser Ala Asp Ser
610                 615                 620

<210> SEQ ID NO 5
<211> LENGTH: 118
<212> TYPE: PRT
<213> ORGANISM: Mus musculus

<400> SEQUENCE: 5

Ser Ala Ala Ser Ala Ser Ala Ala Ser Asp Ile Ser Val Glu Ser Lys
1               5                   10                  15

Glu Ala Thr Ala Cys Thr Val Thr Leu Glu Lys Thr Ser Ala Gly Leu
            20                  25                  30

Gly Phe Ser Leu Glu Gly Gly Lys Gly Ser Leu His Gly Asp Lys Pro
        35                  40                  45

Leu Thr Ile Asn Arg Ile Phe Lys Gly Thr Glu Gln Gly Glu Met Val
    50                  55                  60

Gln Pro Gly Asp Glu Ile Leu Gln Leu Ala Gly Thr Ala Val Gln Gly
65                  70                  75                  80

-continued

```
Leu Thr Arg Phe Glu Ala Trp Asn Val Ile Lys Ala Leu Pro Asp Gly
                85                  90                  95

Pro Val Thr Ile Val Ile Arg Arg Thr Ser Leu Gln Cys Lys Gln Thr
            100                 105                 110

Thr Ala Ser Ala Asp Ser
        115
```

METHODS OF TREATING PULMONARY FIBROSIS

CROSS-REFERENCE TO RELATED APPLICATION

The present application claims the benefit of U.S. Provisional Application Ser. No. 60/863,237, filed 27 Oct. 2006, the entire contents of which are incorporated herein by reference in their entirety.

FIELD OF THE INVENTION

The present invention relates to methods for treating pathological pulmonary conditions. More particularly, the present invention is directed to methods of treating bleomycin associated pulmonary fibrosis by use of IL-16 antagonists.

BACKGROUND OF THE INVENTION

Lung diseases, such as pneumonitis, pulmonary fibrosis or pulmonary sarcoidosis, affect millions of Americans and others worldwide every year. Those afflicted with these pathological pulmonary conditions can feel short of breath, unable to breath, and may die as a result of these diseases.

Author Silas Kane writes of these diseases that:

"The patient always feels like he . . . needs air and is not getting it. It is a slow, torturous death for the patient. Their last months are spent fighting for every breath they take. Caregivers can stand by helplessly watching their loved ones slowly suffocate to death."

See Kane, http://blogcritics.org/archives/2005/09/28/012939.php (Oct. 18, 2006).

Additionally, a significant number of cancer patients receiving bleomycins, such as BLENOXANE® (Bristol-Myers Squib Co., Princeton, N.J.), during chemotherapy develop pulmonary pneumonitis and pulmonary fibrosis after bleomycin administration. Together these pulmonary diseases have significant health and economic impacts. Yet, despite advances in many areas of medicine, comparatively few treatment options and effective therapies are available for these diseases.

Interleukin-16 (IL-16; SEQ ID NO: 2) is a pro-inflammatory cytokine that induces positive chemotaxis of T-lymphocytes, monocytes, eosinophils, and dendritic cells (67 J. Leukocyte Biol. 757 (2000)). IL-16 stimulus also increases IL-1b expression, increases IL-6 expression, and increases IL-15 expression in IL-16 responsive eukaryotic cells (67 J. Leukocyte Biol. 757 (2000)).

IL-16 peptide chain monomers are formed by the Caspase-3 mediated proteolytic processing of a larger 14 kDa precursor molecule (273 J. Biol. Chem. 1144 (1998)). IL-16 monomers form tetrameric peptide chain complexes. These tetrameric IL-16 complexes are believed to be the bioactive form of IL-16 (67 J. Leukocyte Biol. 757 (2000)). Eukaryotic cells that produce IL-16 include cells that express CD4 or CD8, such as T-cells, mast cells, eosinophils, dendritic cells, epithelial cells, fibroblasts, and cells of the cerebellum (67 J. Leukocyte Biol. 757 (2000)). Eukaryotic cells responsive to IL-16 express the CD4 and CD9 peptide chains, but the response to IL-16 may also be independent of these peptide chains (see e.g. 164 J. Immunol. 4429 (2000)).

IL-16 has been reported to play an important role in such diseases as asthma, atopic dermatitis, and rheumatoid arthritis, among others (see e.g. 162 Am. J. Respir. Crit. Care Med. 105 (2000); 109 J. Allergy Clin. Immunol. 681 (2002); 31 J. Rheumatol. 35 (2004). For example, in human patients IL-16 has been shown to be responsible for attracting some asthma inducing cells to the lungs and to play a critical role in triggering asthmatic responses in patients (162 Am. J. Respir. Crit. Care Med. 105 (2000)).

Importantly, the production of cytokines, such as IL-16, may represent a crucial step in promoting the inflammatory immune response and the pulmonary pathologies associated with pneumonitis, pulmonary fibrosis and pulmonary sarcoidosis. However, it has been unclear what, if any, role IL-16 activity plays in these disease conditions.

Thus, a need exists to understand the role of IL-16 in these pathological pulmonary conditions and exploit this role to develop effective treatments for these lung diseases.

SUMMARY OF THE INVENTION

Figure 1:
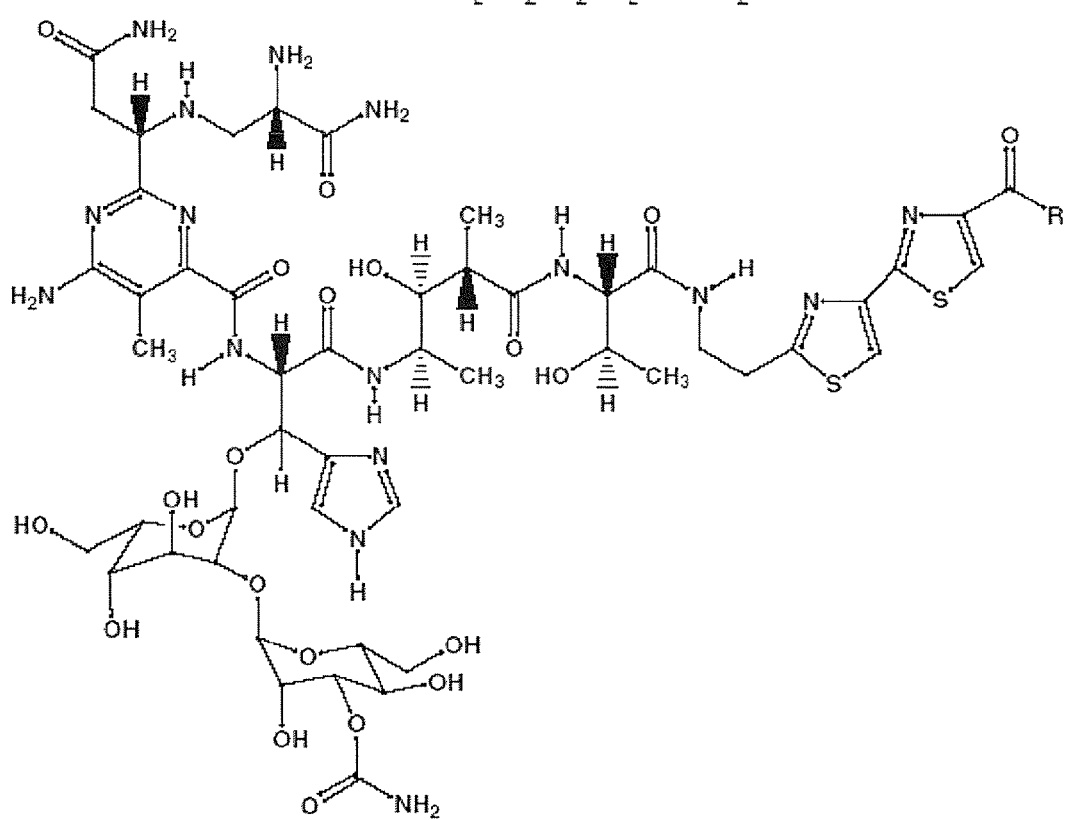
FIG. 1 shows the chemical structure of bleomycin $A_2$ and bleomycin $B_2$.

One aspect of the invention is a method of treating a pathological pulmonary condition comprising the steps of identifying an animal with a pathological pulmonary condition; and administering an IL-16 antagonist to the animal in an amount sufficient to attenuate the pathological pulmonary condition; where the pathological pulmonary condition is selected from the group consisting of pneumonitis, fibrosis and sarcoidosis.

Another aspect of the invention is a method of treating a bleomycin associated pulmonary fibrosis comprising the steps of identifying an animal with a bleomycin associated pulmonary fibrosis; and administering to the animal an IL-16 antagonist or contacting the animal with an IL-16 antagonist in an amount sufficient to attenuate the bleomycin associated pulmonary fibrosis.

In a further aspect of the invention, the method of treating a bleomycin associated pulmonary fibrosis comprises contacting or administering an anti-IL-16 antibody with or to the subject.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a cell" is a reference to one or more cells and includes equivalents thereof known to those skilled in the art.

Unless defined otherwise, all technical and scientific terms used herein have the same meaning as commonly understood by one of ordinary skill in the art to which this invention belongs. Although any compositions and methods similar or equivalent to those described herein can be used in the practice or testing of the invention, exemplary compositions and methods are described herein.

The term "animal" means an organism that is taxonomically classified as belonging to the kingdom Animalia.

The term "IL-16 antagonist" means a molecule that is capable of, directly or indirectly, substantially counteracting, reducing or inhibiting IL-16 biological activity or IL-16 receptor activation. Such antagonists may be, for example, small organic molecules, peptide chains, antibodies, antibody fragments, mimetibodies or polynucleotides.

The term "antibody" as used herein is meant in a broad sense and includes immunoglobulin or antibody molecules including polyclonal antibodies, monoclonal antibodies including murine, human, humanized and chimeric monoclonal antibodies and antibody fragments.

In general, antibodies are proteins or polypeptides that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

The term "antibody fragments" means a portion of an intact antibody, generally at least a portion of the antigen binding or variable region of the intact antibody. Examples of antibody fragments include Fab, Fab', $F(ab')_2$ and Fv fragments, diabodies, single chain antibody molecules and multispecific antibodies formed from at least two intact antibodies.

The term "antigen" means any molecule that has the ability to generate antibodies either directly or indirectly.

Included within the definition of "antigen" is a protein-encoding nucleic acid.

The term "biological activity" means the response of a biological system to a molecule. Such biological systems may be, for example, a cell, a replicable nucleic acid, such as a virus or plasmid, the isolated components of a cell or replicable nucleic acid, or an in vitro system incorporating one or more of these.

The term "bleomycin" means cytotoxic glycopeptide antibiotic bleomycins A and bleomycins B, derivatives of these bleomycins, analogs of these bleomycins, and biologically active metabolites of these bleomycins. Bleomycin sulfate is an example of a bleomycin and comprises bleomycin $A_2$ ($N_1$-[3-(dimethylsulfonio)propyl]-Bleomycinamide) and bleomycin $B_2$ ($N_1$-[4-(aminoiminomethyl)amino]butyl]-bleomycinamide) (FIG. 1). Therapeutic grade bleomycin sulfate is marketed in the U.S. by Bristol-Myers Squib Co. (Princeton, N.J.) under the registered trademark BLENOXANE®.

The term "bleomycin associated pulmonary fibrosis" means a pathological pulmonary condition characterized by pulmonary fibrosis occurring after bleomycin has been administered to an animal.

The term "CDRs" means the complementarity determining region amino acid sequences of an antibody which are the hypervariable regions of immunoglobulin heavy and light chains. See, e.g., Kabat et al. Sequences of Proteins of Immunological Interest, 4th ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

The term "mimetibody" as used herein means a protein having the generic formula (I):

$$(V1\text{-Pep-Lk-}V2\text{-Hg-}C_H2\text{-}C_H3)_{(t)} \qquad (I)$$

where V1 is a portion of an N-terminus of an immunoglobulin variable region, Pep is a polypeptide that binds to, for example, an IL-16 protein, Lk is a polypeptide or chemical linkage, V2 is a portion of a C-terminus of an immunoglobulin variable region, Hg is a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10. A mimetibody can mimic properties and functions of different types of immunoglobulin molecules such as IgG1, IgG2, IgG3, IgG4, IgA, IgM, IgD and IgE dependent on the heavy chain constant domain amino acid sequence present in the construct. In some mimetibody embodiments, V1 may be absent. A mimetibody antagonist of the present invention affects IL-16 biological activity through binding to IL-16 and preventing IL-16 mediated biological signaling.

The term "monoclonal antibody" (mAb) means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., Nature 256:495-497 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Humanized mAbs having CDRs derived from a non-human donor immunoglobulin (typically murine) and the remaining immunoglobulin-derived parts of the molecule being derived from one or more human immunoglobulins, optionally having altered framework support residues to preserve binding affinity, can be obtained by the techniques disclosed in Queen et al., *Proc. Natl. Acad. Sci. (USA)*, 86:10029-10032 (1989) and Hodgson et al., *Bio/Technology*, 9:421 (1991).

Exemplary human framework sequences useful for humanization are disclosed at, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; wwW.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~-yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; http://www.bioinf.org.uk/abs; antibody.bath.ac.uk; www.unizh.ch; www.cryst.bbk.ac.uk/~ubcgo7s; www.nimr.mrc.ac.uk/CC/ccaewg/ccaewg.html; wwW.path.cam.ac.uk/~mrc7/humanisation/TAHHP.html; www.ibt.unam.mx/vir/structure/stat_aim.html; www.biosci.missouri.edu/smithgp/index.html; www.jerini.de; and Kabat et al., Sequences of Proteins of Immunological Interest, U.S. Dept. Health (1987), each entirely incorporated herein by reference.

Fully human mAbs lacking any non-human sequences can be prepared from human immunoglobulin transgenic mice by techniques referenced in, e.g., Lonberg et al., *Nature* 368: 856-859 (1994); Fishwild et al., *Nature Biotechnology* 14:845-851 (1996) and Mendez et al., *Nature Genetics* 15:146-156 (1997). Human mAbs can also be prepared and optimized from phage display libraries by techniques referenced in, e.g., Knappik et al., *J. Mol. Biol.* 296:57-86 (2000) and Krebs et al., *J. Immunol. Meth.* 254:67-84 (2001).

The term "fibrosis" means a state of disease or abnormal tissue function characterized by the formation of fibrous tissue, fibroids, or fibrous degeneration.

The term "IL-16" means a peptide chain comprising an amino acid sequence with at least 70% identity to amino acid residues 1 to 631 of SEQ ID NO: 1 or a peptide chain comprising an amino acid sequence with at least 79% identity to amino acid residues 1-121 of SEQ ID NO: 2. "IL-16" is an acronym for "Interleukin 16." Identity between two peptide chains can be determined by pair-wise amino acid sequence alignment using the default settings of the AlignX module of Vector NTI v.9.0.0 (Invitrogen Corp., Carslbad, Calif.). AliquX uses the CLUSTALW algorithm to perform pair-wise amino acid sequence alignments.

The term "peptide chain" means a molecule that comprises at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The term "pathological pulmonary condition" means a state of disease or abnormal function affecting at least one portion of one lung.

The term "pulmonary" means relating to, occurring in, or affecting at least one portion of one lung.

The term "pneumonitis" means inflammation of at least one portion of one lung.

The term "phosphorylated STAT-6 proxy," means a phosphorylated peptide chain with at least 80% identity to amino acid residues 1 to 846 of SEQ ID NO: 3, a peptide chain expressed by activating the regulatory region of a gene responsive to a phosphorylated peptide chain with at least 80% identity to amino acid residues 1 to 846 of SEQ ID NO: 3, or a nucleic acid transcribed by activating the regulatory region of a gene responsive to a phosphorylated peptide chain with at least 80% identity to amino acid residues 1 to 846 of SEQ ID NO: 3. A phosphorylated STAT-6 proxy can be used as an indicator of STAT-6 peptide chain activation. "STAT" is an acronym for "signal transducers and activators of transcription." STAT-6 is an intracellular peptide chain that is phosphorylated, typically on a tyrosine residue, in response to signaling by interleukins such as IL-3, IL-4, and IL-13. Phosphorylation of STAT-6 activates STAT-6. Activated STAT-6 induces transcription of interleukin responsive genes by binding discrete response elements in DNAs. Regulatory regions in nucleic acids, such as DNAs, may comprise, or consist of, such discrete response elements. Activated STAT-6 induces, for example, transcription of the genes encoding *Homo sapiens* BCL2-like 1 isoform 2 and BCL-X(L).

The term "sarcoidosis" means a state of disease or abnormal tissue function characterized by the formation of granulomas.

The methods of the invention are useful for the treatment of pathological pulmonary conditions and bleomycin sulfate associated pulmonary fibrosis in animals including humans.

One aspect of the invention is a method of treating a pathological pulmonary condition comprising the steps of identifying an animal with a pathological pulmonary condition; and administering an IL-16 antagonist to the animal in an amount sufficient to attenuate the pathological pulmonary condition; where the pathological pulmonary condition is selected from the group consisting of pneumonitis, fibrosis and sarcoidosis.

An animal with a pathological pulmonary condition can be identified using such diagnostic techniques as assessment of symptoms presented by the animal, pulmonary function tests, radiant energy based imaging, or biopsy. Such animals may be humans (*Homo sapiens*) or mice (*Mus musculus*) or any animal in which a pathological pulmonary condition can be attenuated with an IL-16 antagonist.

Symptoms of pathological pulmonary conditions include shortness of breath (dyspnea), shortness of breath on exertion, nonproductive cough, and "velcro-type" inspiratory crackles on chest examination, finger clubbing, cyanosis, *cor pulmonale*, fine rails or other symptoms of pneumonitis, fibrosis and sarcoidosis.

Typically, pulmonary function tests will reveal a restrictive pattern. For example, the coefficient of retraction (maximal static transpulmonary pressure/total lung capacity) may be increased, the diffusing capacity for carbon monoxide ($DL_{CO}$) may be reduced, or analysis of arterial blood gases may show hypoxemia and low arterial $CO_2$ levels ($Pa_{CO2}$) which may be exaggerated by, or associated with, exercise. Total lung volume may be decreased and vital capacity may also be decreased. Sequential measurement of pulmonary diffusion capacity for carbon monoxide ($DL_{CO}$) may reveal a $DL_{CO}$ value that has decreased to under 36% of an initial measurement in the sequence.

Radiant energy based imaging techniques, such as conventional X-ray imaging (Roentgenograms), computed tomography X-ray imaging, and magnetic resonance imaging, may reveal nonspecific patchy opacities usually in the lower lung fields, small cystic lesions, honeycombing, granuloma formation, diffuse reticular opacities in the lower lung zones, diffuse or patchy ground-glass haziness, evidence of reduced lung volumes, signs of pulmonary hypertension, or other evidence of pneumonitis, fibrosis and sarcoidosis.

Biopsy of the lungs and additional analysis of biopsy samples may reveal increased interstitial collagen deposition, increased total soluble collagen levels, small cystic lesions, honeycombing, granuloma formation, evidence of reduced lung volumes, signs of pulmonary hypertension, bronchiolar squamous metaplasia, reactive macrophages, atypical alveolar epithelial cells, fibrinous edema, interstitial fibrosis, capillary changes, fibrinous exudation into the alveoli producing a change similar to hyaline membrane formation, a diffuse interstitial fibrosis resembling the Hamman-Rich syndrome, or other evidence of pneumonitis, fibrosis and sarcoidosis.

IL-16 antagonists useful in the methods of the invention may be, for example, small organic molecules, peptide chains, antibodies, antibody fragments, mimetibodies or polynucleotides capable of inhibiting IL-16 mediated signaling. Such IL-16 antagonists may have the properties of binding an IL-16 or an IL-16 receptor and inhibiting IL-16 mediated biological signaling. Silencing RNAs and antisense RNAs are examples of polynucleotides capable of inhibiting IL-16 mediated signaling. Exemplary mechanisms by which IL-16 signaling may be inhibited by such antagonists include inhibition of kinase activity, transcript reduction or receptor binding. Other antagonists capable of inhibiting IL-16 biological activity by other mechanisms are also useful in the methods of the invention.

In the methods of the invention an IL-16 antagonist may be administered by any mode of administration or route that delivers the IL-16 antagonist to the host. For example, IL-16 antagonists may be administered parenterally, i.e., subcutaneously, intramuscularly, intradermally, intravenously or intranasally. Alternatively, IL-16 antagonists may be administered enterically by, for example, anal or oral routes of administration.

In the methods of the invention, the IL-16 antagonist may be administered singly or in combination with at least one other molecule. Such additional molecules may be other IL-16 antagonist molecules or molecules with a therapeutic benefit not mediated by IL-16 biological activity or IL-16 receptor signaling. Antibiotics, antivirals, other immunomodulators, other anti-inflammatory agents, leukotriene antagonists, β2 agonists and muscarinic receptor antagonists are examples of such additional molecules.

IL-16 antagonists useful in the methods of the invention may be prepared as pharmaceutical compositions containing an effective amount of the IL-16 antagonist as an active ingredient in a pharmaceutically acceptable carrier. An aqueous suspension or solution containing the IL-16 antagonist, preferably buffered at physiological pH, in a form ready for injection is preferred. An aqueous solution comprising an IL-16 antagonist, such as mAb 14.1, in phosphate buffered saline (PBS) is one example of such a pharmaceutical composition. Pharmaceutical compositions for parenteral administration will typically comprise a solution of an IL-16 antagonist or a cocktail thereof in a pharmaceutically acceptable carrier, preferably, an aqueous carrier. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The pharmaceutical compositions may contain pharmaceutically acceptable auxiliary substances as required to approximate physiological conditions, such as pH adjusting and buffering agents, etc. The concentration of the IL-16 antagonist in such pharmaceutical formulation can vary widely, i.e., from less than about 0.5%, usually at or at least about 1% to as much as 15 or 20% by weight and will be selected primarily based on fluid volumes, viscosities, solubities, etc. according to the particular mode of administration selected.

The peptide chain IL-16 antagonists useful in the methods of the invention can also be lyophilized for storage and reconstituted in a suitable carrier, such as an aqueous solution, prior to use. This technique has been shown to be effective with conventional immunoglobulins and other peptide chain preparations and art-known lyophilization and reconstitution techniques can be readily employed.

Thus, a pharmaceutical composition useful in the methods of the invention for intramuscular injection could be prepared to contain 1 mL sterile buffered water, and between about 1 ng to about 100 mg, e.g., about 50 ng to about 30 mg or, more preferably, about 5 mg to about 25 mg, of an IL-16 antagonist. Similarly, a pharmaceutical composition of the invention for intravenous infusion could be made up to contain about 250 ml of sterile Ringer's solution, and about 1 mg to about 30 mg and, preferably, 5 mg to about 25 mg of an IL-16 antagonist. Actual methods for preparing parenterally administrable compositions are well known and are described in more detail in, for example, "Remington's Pharmaceutical Science", 15th ed., Mack Publishing Company, Easton, Pa. IL-16 antagonists useful in the methods of the invention, when in a pharmaceutical composition, can be present in unit dose forms.

Amounts of a given IL-16 antagonist sufficient to treat a given pathological pulmonary condition can be readily determined. Such appropriate therapeutically effective doses can be determined readily by those of skill in the art. For example, several different amounts of a given IL-16 antagonist can be administered to different individuals and the amount producing the maximum attenuation of the symptoms of the pathological pulmonary condition can be selected as the dose. A determined dose may, if necessary, be repeated at appropriate time intervals selected as appropriate by a physician or other performing the methods of the invention during the treatment period. For example, administration can occur on a first day, then again 5 days later, and again 11 days later.

In one embodiment of the method of the invention, the IL-16 antagonist is an isolated antibody reactive with IL-16. Such antibodies can be readily generated using techniques, such as hybridoma and CDR grafting techniques, well known in the art. Peptide chains comprising SEQ ID NO: 1 or SEQ ID NO: 2 or a portion of these sequences can be used as an immunogen and to identify antibodies that are IL-16 antagonists. IL-16 antagonist antibodies may be identified using the assay methods disclosed in U.S. provisional patent applications 60/827,313 and 60/804,468, the entire disclosure of each of which is incorporated herein by reference.

For example, an IL-16 antagonist antibody can be identified using a method of detecting a molecule that decreases IL-16 biological activity in a sample comprising the steps of providing a first population of eukaryotic cells surrounded by media and responsive to IL-16 biological activity with a first test sample; providing a second population of eukaryotic cells surrounded by media and responsive to IL-16 biological activity with a positive control sample containing biologically active IL-16; measuring the amount of a phosphorylated STAT-6 proxy produced by the first and second populations of eukaryotic cells; and comparing the amount of a phosphorylated STAT-6 proxy produced by the first and second populations of eukaryotic cells, wherein a smaller amount of a phosphorylated STAT-6 proxy produced by the first population of eukaryotic cells relative to the phosphorylated STAT-6 proxy level produced by the second population of eukaryotic cells indicates the presence of a molecule that decreases IL-16 biological activity in the test sample. Phosphorylated *Homo sapiens* STAT-6 (SEQ ID NO: 3) is an example of a phosphorylated STAT-6 proxy. Those skilled in the art will recognize other suitable phosphorylated STAT-6 proxies. A decrease in RANTES proxy can also be used as a measure of IL-16 biological activity using similar methods to those described above as known to those of ordinary skill in the art. Eukaryotic cells useful in such assay methods include *Homo sapiens* peripheral blood mononuclear cells isolated using standard methods and *Homo sapiens* derived THP-1 monocyte cells (ATCC® Number: TIB-202™; American Type Culture Collection (ATCC), Manassas, Va.).

Exemplary antibody IL-16 antagonists useful in the methods of the invention may be antibodies of the IgG, IgD, IgGA or IgM isotypes. Additionally, such antagonist antibodies can be post-translationally modified by processes, such as glycosylation, isomerization, aglycosylation or non-naturally occurring covalent modification, such as the addition of polyethylene glycol moieties (pegylation) and lipidation. Such modifications may occur in vivo or in vitro. Fully human, humanized and affinity-matured antibody molecules or antibody fragments are within the scope of the invention as are mimetibodies, fusion proteins and chimeric proteins.

IL-16 antagonists useful in the methods of the invention may bind IL-16 with a $K_d$ less than or equal to about $10^{-7}$, $10^{-8}$, $10^{-9}$, $10^{-10}$, $10^{-11}$ or $10^{-12}$ M. The affinity of a given molecule for an IL-16 protein can be determined experimentally using any suitable method. Such methods may utilize Biacore or KinExA instrumentation, ELISA or competitive binding assays known to those skilled in the art.

IL-16 antagonist antibody molecules binding a given IL-16 with a desired affinity can be selected from libraries of variants or fragments by techniques including antibody affinity maturation and other art recognized techniques suitable for non-antibody molecules.

In another embodiment of the method of the invention, the isolated antibody competes with the monoclonal antibody 14.1 for binding of IL-16. mAb 14.1 is murine 19G2A monoclonal antibody that specifically binds *Mus musculus* IL-16 (SEQ ID NO: 4 and SEQ ID NO: 5) and antagonizes the biological activity of the *Mus musculus* IL-16 cytokine. mAb 14.1 was originally raised against recombinantly expressed *Homo sapiens* IL-16 and binds to an epitope present in the 130 carboxy terminal amino acid residues of *Homo sapiens* pro-IL-16. Importantly, mAb 14.1 cross reacts with the *Mus musculus* IL-16 cytokine. mAb 14.1 binds both the precursor (pro-IL-16) and mature forms of IL-16.

Antibodies that compete with mAb 14.1 for binding of IL-16 can be identified using standard competitive binding assays well known in the art. In such assays, binding of mAb 14.1 to its epitope on a given IL-16 peptide chain produces a detectable signal while providing an antibody that competes with mAb 14.1 for binding of a given IL-16 peptide chain will cause this detectable signal to decrease relative to appropriate control samples.

Isolated antibodies that compete with the monoclonal antibody 14.1 for binding of IL-16 are identified using the following steps. First, mAb 14.1 is labeled (e.g., radiolabeled) and IL-16 peptide chains are immobilized on an insoluble substrate. Immobilized IL-16 may be presented as a monomeric molecule or as part of a multimeric peptide chain complex, such as the tetrameric IL-16 peptide chain complex comprising four IL-16 monomers. Second, a positive control sample is prepared in which a first quantity of labeled mAb 14.1 is incubated with the immobilized IL-16 for a fixed period of time (e.g., 15 min.). Third, a test sample is prepared by incubating a second quantity of an unlabeled or differentially labeled antibody preparation with immobilized IL-16 followed for a fixed period of time (e.g., 15 min.). Fourth, a first quantity of labeled mAb 14.1 is added to the test sample and the test sample is incubated for a fixed period of time (e.g., 15 min). The final volumes of the positive control samples and test samples should be the same.

Fifth, an appropriate solution (e.g., PBS) is used to wash the insoluble substrate in the positive control and test samples. This step removes antibody molecules that have not bound the immobilized IL-16. Sixth, the amounts of labeled mAb 14.1 bound to the insoluble substrate in the positive control sample and test samples are measured. The antibody preparation included in the test sample is an IL-16 antagonist antibody that competes with the monoclonal antibody 14.1 for binding of IL-16 when the amount of labeled mAb 14.1 bound to the insoluble substrate in the test sample is less than the amount of mAb 14.1 bound to the insoluble substrate in the positive control sample.

In another embodiment of the method of the invention, the amount of the IL-16 antagonist sufficient to attenuate the pathological pulmonary condition is 25 milligrams per kilogram of animal body weight.

Another aspect of the invention is a method of treating a bleomycin sulfate associated pulmonary fibrosis comprising the steps of identifying a subject (e.g., an animal) with a bleomycin sulfate associated pulmonary fibrosis; and administering an IL-16 antagonist to the subject in an amount sufficient to attenuate the bleomycin sulfate associated pulmonary fibrosis.

A subject with a bleomycin associated pulmonary fibrosis can be identified using such diagnostic techniques as assessment of symptoms presented by the subject, pulmonary function tests, radiant energy based imaging, or biopsy. Such subjects (animals) may be humans (*Homo sapiens*) or mice (*Mus musculus*) or any animal in which a bleomycin sulfate associated pulmonary fibrosis can be attenuated with an IL-16 antagonist.

Symptoms of bleomycin associated pulmonary fibrosis include shortness of breath (dyspnea), shortness of breath on exertion, nonproductive cough, and "velcro-type" inspiratory crackles on chest examination, finger clubbing, cyanosis, *cor pulmonale*, fine rails or other symptoms of fibrosis after bleomycin has been administered to a subject. In many instances, such symptoms may occur within 14 days after bleomycin has been administered.

Typically, pulmonary function tests will reveal a restrictive pattern. For example, the coefficient of retraction (maximal static transpulmonary pressure/total lung capacity) may be increased, the diffusing capacity for carbon monoxide ($DL_{CO}$) may be reduced, or analysis of arterial blood gases may show hypoxemia and low arterial $CO_2$ levels ($Pa_{CO2}$) which may be exaggerated by, or associated with, exercise. Total lung volume may be decreased and vital capacity may also be decreased. Sequential measurement of pulmonary diffusion capacity for carbon monoxide ($DL_{CO}$) may reveal a $DL_{CO}$ value that has decreased to under 36% of an initial measurement in the sequence.

Radiant energy based imaging techniques, such as conventional X-ray imaging (Roentgenograms), computed tomography X-ray imaging, and magnetic resonance imaging, may reveal nonspecific patchy opacities usually in the lower lung fields, small cystic lesions, honeycombing, granuloma formation, diffuse reticular opacities in the lower lung zones, diffuse or patchy ground-glass haziness, evidence of reduced lung volumes, signs of pulmonary hypertension, or other evidence of fibrosis after bleomycin has been administered to a subject. In many instances, such symptoms may occur within 14 days after bleomycin has been administered.

Biopsy of the lungs and additional analysis of biopsy samples may reveal increased interstitial collagen deposition, increased total soluble collagen levels, small cystic lesions, honeycombing, granuloma formation, evidence of reduced lung volumes, signs of pulmonary hypertension, bronchiolar squamous metaplasia, reactive macrophages, atypical alveolar epithelial cells, fibrinous edema, interstitial fibrosis, capillary changes, fibrinous exudation into the alveoli producing a change similar to hyaline membrane formation, a diffuse interstitial fibrosis resembling the Hamman-Rich syndrome, or other evidence of fibrosis after bleomycin has been administered to a subject.

In many instances, such symptoms may occur within 14 days after bleomycin has been administered.

Amounts of a given IL-16 antagonist sufficient to treat a given bleomycin associated pulmonary fibrosis can be readily determined. Such appropriate therapeutically effective doses can be determined readily by those of skill in the art. For example, several different amounts of a given IL-16 antagonist can be administered to different individuals and the amount producing the maximum attenuation of the symptoms of the bleomycin associated pulmonary fibrosis can be selected as the dose. A determined dose may, if necessary, be repeated at appropriate time intervals selected as appropriate by a physician or other performing the methods of the invention during the treatment period. For example, administration can occur on a first day, then again 5 days later, and again 11 days later.

In one embodiment of the method of the invention, the IL-16 antagonist is an isolated antibody reactive with IL-16.

In another embodiment of the method of the invention, the isolated antibody competes with the monoclonal antibody 14.1 for binding of IL-16.

In another embodiment of the method of the invention, the therapeutically effective amount of the IL-16 antagonist sufficient to attenuate the bleomycin associated pulmonary fibrosis is 25 milligrams per kilogram of subject body weight.

The present invention is further described with reference to the following examples. These examples are merely to illustrate aspects of the present invention and are not intended as limitations of this invention.

EXAMPLE 1

Figure 2:
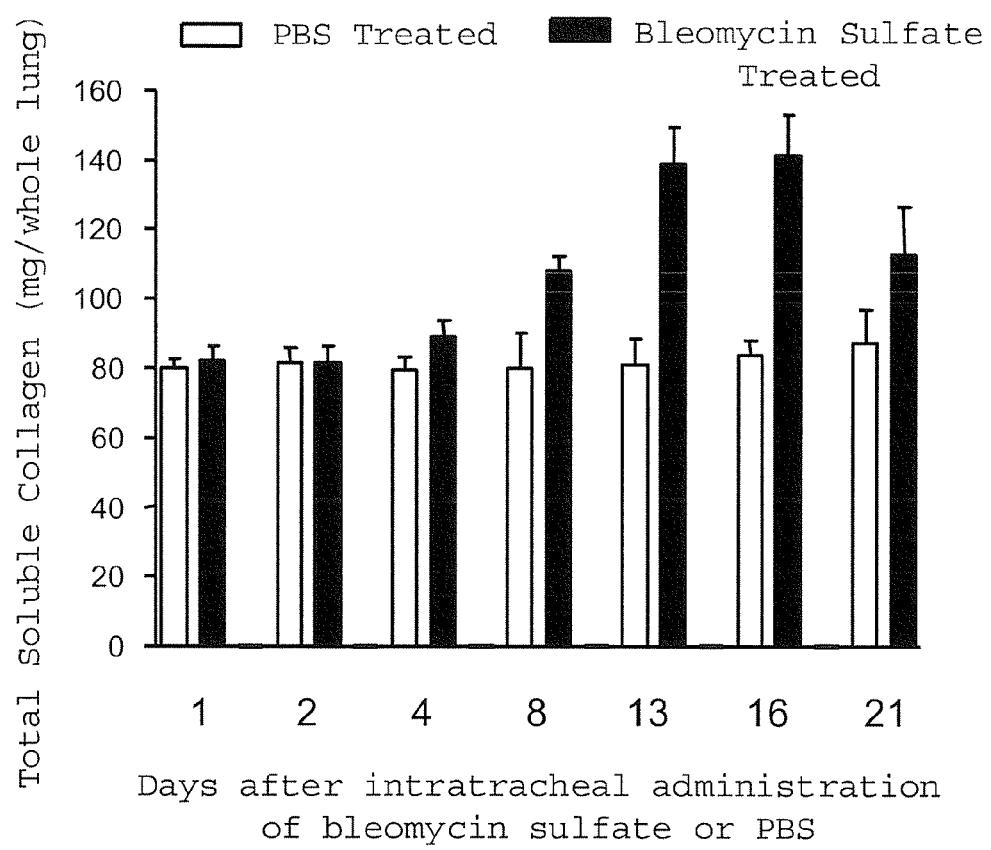
FIG. 2 is a graph showing that increased soluble collagen levels in mouse lung tissues are a symptom of bleomycin sulfate associated pulmonary fibrosis.

Increased Soluble Collagen Levels in Lung Tissues is a Symptom of Pulmonary Fibrosis Increased soluble collagen levels in fibrotic lung tissues is a symptom of pulmonary fibrosis. Soluble collagen levels are increased in fibrotic lung tissues relative to normal lung tissues in a mouse model of bleomycin sulfate associated pulmonary fibrosis (FIG. 2).

Bleomycin sulfate is a chemotherapeutic drug commonly used in the treatment of cancer. Bleomycin sulfate treatment in human patients can induce pulmonary fibrosis. Administration of 0.05 U of bleomycin sulfate to mice induces pulmonary fibrosis and symptoms of fibrosis can be observed in lung tissues as late as 21 days after treatment. Importantly, expression of collagen proteins in the lungs increases as pulmonary fibrosis progresses (see e.g. Águas et al. 12 Scanning Microsc. 487 (1998)). Consequently, total soluble collagen levels in fibrotic lung tissues are elevated relative to normal lung tissues.

Pulmonary fibrosis was induced in female C57/Bl6 mice by intratracheal administration of 0.05 U of bleomycin sulfate (Sigma-Aldrich Inc., St. Louis, Mo.) in 50 µL of sterile phosphate buffered saline (PBS) at pH 7.4 on Day 0. Negative control mice received only 50 µL of sterile PBS at pH 7.4 on Day 0. Animals receiving bleomycin sulfate or PBS alone were then sacrificed on Days 1, 2, 4, 8, 13, 16, and 21 in compliance with institutional animal care and use guidelines.

Lungs were then harvested from the sacrificed animals and homogenized in 1 mL PBS containing Complete™ Protease Inhibitor Cocktail (Roche Applied Science Inc., Indianapolis, Ind.). Complete™ Protease Inhibitor Cocktail was provided in the quantity directed by the manufacturer. Lung homogenates were then centrifuged for 10 minutes at 1300 RPM to pellet insoluble materials and supernatants containing soluble materials were collected. Total soluble collagen levels in the supernatants were measured using the Sircol™ Soluble Collagen Assay System (BiColor Ltd., Belfast, IR) as directed by the manufacturer.

The data in FIG. 2 shows total soluble collagen levels are detectably increased in fibrotic lung tissues from bleomycin sulfate treated mice relative to nonfibrotic lung tissues from untreated mice as early as 4 days after induction of fibrosis. This data indicates increased soluble collagen levels in lung tissues is a symptom of pulmonary fibrosis and is consistent with previous reports in the literature.

EXAMPLE 2

Figure 3:
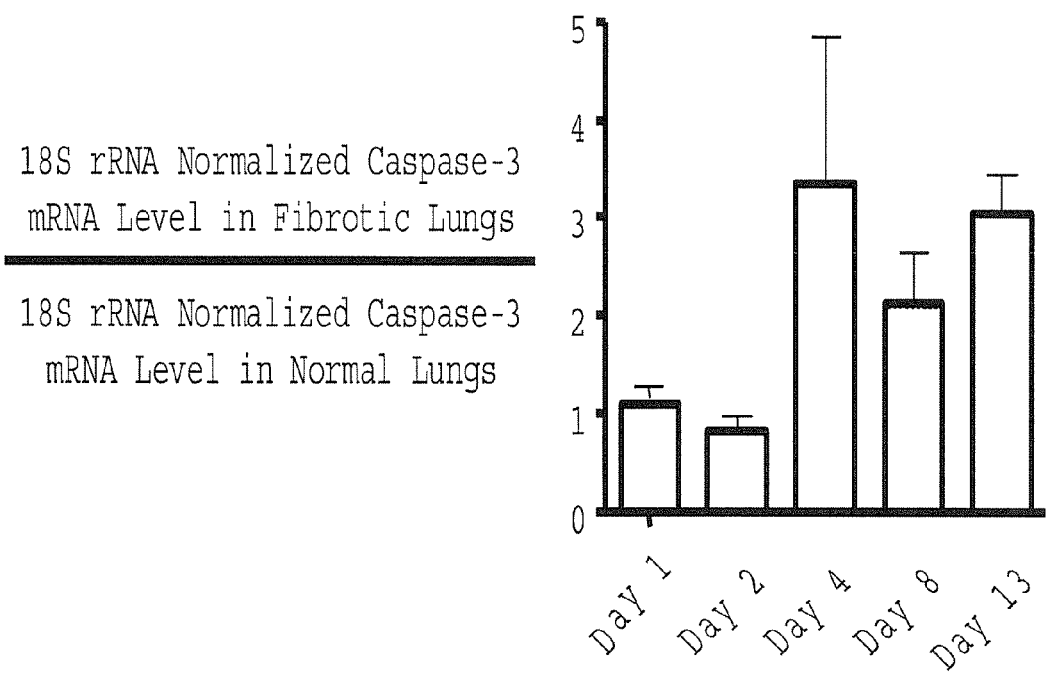
FIG. 3 is a graph showing that Caspase-3 gene transcript levels are increased in fibrotic lung tissues relative to normal lung tissues in a mouse model of bleomycin sulfate associated pulmonary fibrosis.

Caspase-3 Gene Transcript Levels are Increased in Fibrotic Lung Tissues Relative to Normal Lung Tissues Caspase-3 gene transcript levels are increased in fibrotic lung tissues relative to normal lung tissues in a mouse model of bleomycin sulfate associated pulmonary fibrosis (FIG. 3).

Total RNA was extracted from the fibrotic lungs of bleomycin sulfate treated mice and the normal lungs of negative control mice receiving PBS. Mice were treated as described in Example 1 above and lungs were harvested at Day 1, Day 2, Day 4, Day, 8, and Day 13. RNA was extracted using standard methods. Real time polymerase chain reaction (RT-PCR) techniques were then used to convert extracted Caspase-3 gene mRNA transcripts and 18S rRNA transcript in the samples into cDNAs. TaqMan® Low Density Array Cards (Applied Biosystems Inc., Foster City, Calif.) containing *Mus musculus* Caspase-3 mRNA and 18S rRNA specific primers and probes were used as directed by the manufacturer to generate and detect Caspase-3 specific cDNAs using standard methods. Detected levels of Caspase-3 mRNA and 18S rRNA specific cDNAs in each sample were then measured.

Measured Caspase-3 gene transcript levels in each sample were normalized to 18S gene transcript levels in the sample. Normalized Caspase-3 gene transcript measurements in fibrotic lungs harvested from bleomycin sulfate treated mice were then divided by normalized Caspase-3 gene transcript measurements from normal lungs harvested from negative control mice receiving PBS. Consequently, data in FIG. 3 represents the fold increase in 18S rRNA normalized Caspase-3 gene transcript levels in fibrotic lungs from bleomycin sulfate treated mice relative to 18S rRNA normalized Caspase-3 gene transcript levels in normal lungs from mice receiving PBS.

The data in FIG. 3 shows that Caspase-3 gene transcript levels are increased in fibrotic lung tissues relative to normal lung tissues in a mouse model of bleomycin sulfate associated pulmonary fibrosis. The Caspase-3 gene is required for proteolytic processing of immature pro-IL-16 to generate the bioactive, mature form of IL-16. The data here (FIG. 3) suggests that production of bioactive, mature IL-16 may be increased in fibrotic lung tissues relative to normal lung tissues as a result of increased Caspase-3 gene activation during pulmonary fibrosis.

EXAMPLE 3

Figure 4:
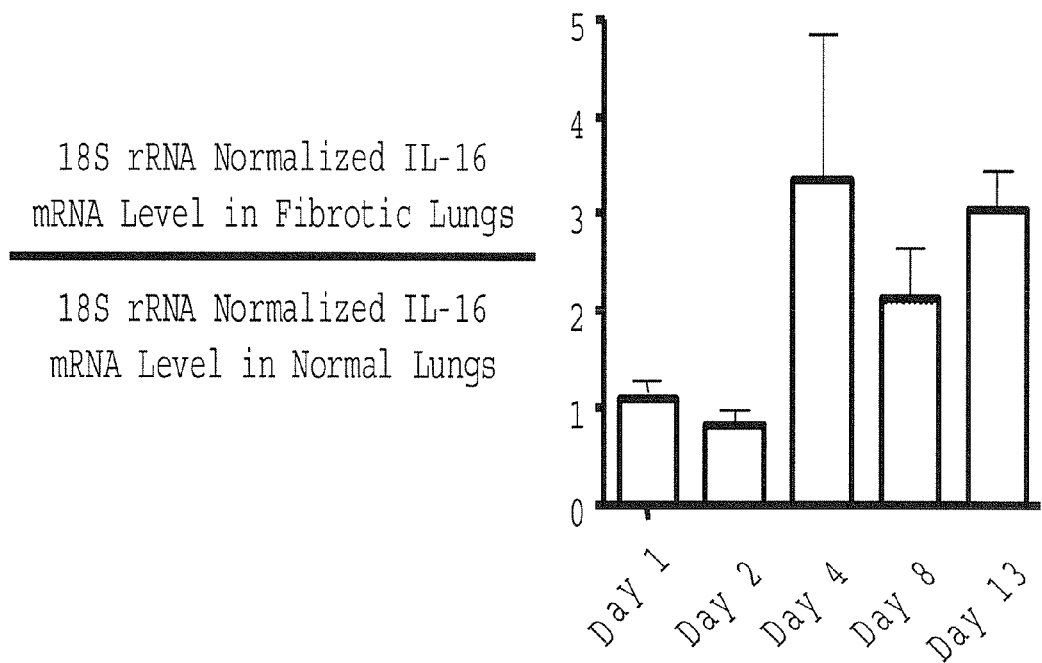
FIG. 4 is a graph showing that IL-16 gene transcript levels are increased in fibrotic lung tissues relative to normal lung tissues in a mouse model of bleomycin sulfate associated pulmonary fibrosis.

IL-16 Gene Transcript Levels are Increased in Fibrotic Lung Tissues Relative to Normal Lung Tissues IL-16 gene transcript levels are increased in fibrotic lung tissues relative to normal lung tissues in a mouse model of bleomycin sulfate associated lung fibrosis (FIG. 4).

Total RNA was extracted from the fibrotic lungs of bleomycin sulfate treated mice and the normal lungs of negative control mice receiving PBS. Mice were treated as described in Example 1 above and lungs were harvested at Day 1, Day 2, Day 4, Day, 8, Day 13, Day 16, and Day 21. RNA was extracted using standard methods. Real time polymerase chain reaction (RT-PCR) techniques were then used to convert extracted IL-16 gene mRNA transcripts and 18S rRNA transcript in the samples into cDNAs. TaqMan® Low Density Array Cards (Applied Biosystems Inc., Foster City, Calif.) containing *Mus musculus* IL-16 mRNA and 18S rRNA specific primers and probes were used as directed by the manufacturer to generate and detect IL-16 specific cDNAs using standard methods. Detected levels of IL-16 mRNA and 18S rRNA specific cDNAs in each sample were then measured.

Measured IL-16 gene transcript levels in each sample were normalized to 18S gene transcript levels in the sample.

Normalized IL-16 gene transcript measurements in fibrotic lungs harvested from bleomycin sulfate treated mice were then divided by normalized IL-16 gene transcript measurements from normal lungs harvested from negative control mice receiving PBS. Consequently, data in FIG. 4 represents the fold increase in 18S rRNA normalized IL-16 gene transcript levels in fibrotic lungs from bleomycin sulfate treated mice relative to 18S rRNA normalized IL-16 gene transcript levels in normal lungs from mice receiving PBS.

The data in FIG. 4 shows that IL-16 gene transcript levels are increased in fibrotic lung tissues relative to normal lung tissues in a mouse model of bleomycin sulfate associated lung fibrosis. The data here (FIG. 4) suggests that production of bioactive, mature IL-16 is increased in fibrotic lung tissues relative to normal lung tissues. This is consistent with the increased transcription of the Caspase-3 gene in fibrotic lung tissues relative to normal lung tissues observed above (FIG. 3). Importantly, this data indicates that antagonists of IL-16 activity may be useful in treating pulmonary fibrosis and associated symptoms.

EXAMPLE 4

IL-16 Antagonist Treatment Decreases Pulmonary Fibrosis Symptoms in Lung Tissue

Figure 5:
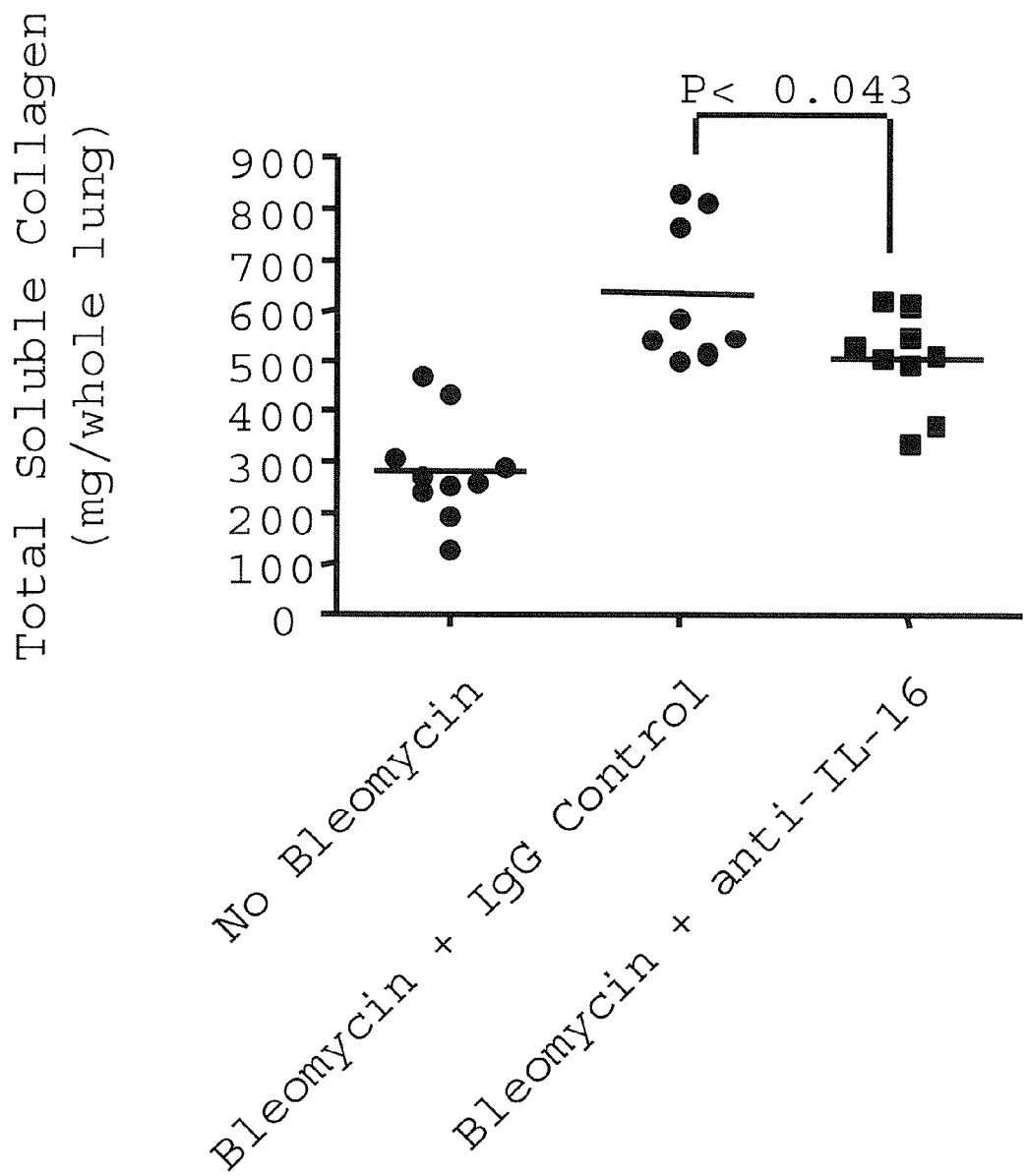
FIG. 5 is a graph showing that treatment with an IL-16 antagonist monoclonal antibody (mAb) decreases soluble collagen levels in fibrotic lung tissues of treated animals relative to fibrotic lung tissues in untreated animals in a mouse model of bleomycin sulfate associated pulmonary fibrosis.

IL-16 antagonist treatment decreases pulmonary fibrosis symptoms in lung tissues. Treatment with an IL-16 antagonist monoclonal antibody (mAb) decreases soluble collagen levels in fibrotic lung tissues of treated animals relative to fibrotic lung tissues in untreated animals in a mouse model of bleomycin sulfate associated pulmonary fibrosis (FIG. 5).

Pulmonary fibrosis was induced in female C57/Bl6 mice by intratracheal administration of 0.05 U of bleomycin sulfate (Sigma-Aldrich Inc., St. Louis, Mo.) in 50 µL of sterile PBS at pH 7.4 on Day 0 as described in Example 1 above. Negative control mice received only 50 µL of sterile PBS at pH 7.4 on Day 0 as described in Example 1 above.

Mock treated mice received a 0.5 mg per mouse dose of a negative control IgG mAb that does not bind IL-16 on Days 1, 6, and 12 after administration of bleomycin sulfate. Treated mice received a 0.5 mg per mouse dose of a mAb 14.1 on Days 1, 6, and 12 after administration of bleomycin sulfate. mAb 14.1 is murine IgG2A monoclonal antibody that specifically binds *Mus musculus* IL-16 (SEQ ID NO: 4 and SEQ ID NO: 5) and antagonizes the biological activity of the *Mus musculus* IL-16 cytokine. mAb 14.1 was originally raised against recombinantly expressed *Homo sapiens* IL-16 and binds to an epitope present in the 130 carboxy terminal amino acid residues of *Homo sapiens* pro-IL-16. Importantly, mAb 14.1 cross reacts with the *Mus musculus* IL-16 cytokine. mAb 14.1 binds both the precursor (pro-IL-16) and mature forms of IL-16.

Animals were sacrificed on Day 14 in compliance with institutional animal care and use guidelines. Lungs were harvested, homogenates prepared, supernatants isolated and total soluble collagen levels were measured as described in Example 1 above.

The data depicted in FIG. 5 shows that treatment with an IL-16 antagonist monoclonal antibody (mAb) decreases soluble collagen levels in fibrotic lung tissues of treated animals relative to fibrotic lung tissues in untreated animals in a mouse model of bleomycin sulfate associated pulmonary fibrosis. This data indicates that IL-16 antagonists can be used to treat pulmonary fibrosis and associated symptoms. Statistical analysis using the unpaired Student T-test with Welch's correction demonstrated that there was a statistically significant difference at a P value of less than 0.043 between the soluble collagen levels in fibrotic lung tissues of treated animals and soluble collagen levels in fibrotic lung tissues in untreated animals in a mouse model of bleomycin sulfate associated pulmonary fibrosis (FIG. 5).

The present invention now being fully described, it will be apparent to one of ordinary skill in the art that many changes and modifications can be made thereto without departing from the spirit or scope of the appended claims.

The invention claimed is:

1. A method of treating pulmonary fibrosis comprising the steps of:
   a) identifying a subject with pulmonary fibrosis; and
   b) administering or contacting an IL-16 antagonist to the subject in an amount sufficient to attenuate the pathological pulmonary condition;
   wherein the IL-16 antagonist is an isolated antibody reactive with IL-16.

2. The method of claim 1, wherein the amount of the isolated antibody sufficient to attenuate the pulmonary fibrosis is 25 milligrams per kilogram of subject body weight.

3. A method of treating a bleomycin associated pulmonary fibrosis comprising the steps of:
   a) identifying a subject with a bleomycin associated pulmonary fibrosis; and
   b) administering or contacting an IL-16 antagonist to the subject in an amount sufficient to attenuate the bleomycin associated pulmonary fibrosis, wherein the IL-16 antagonist is an isolated antibody reactive with IL-16.

4. The method of claim 3, wherein the amount of the isolated antibody sufficient to attenuate the bleomycin associated pulmonary fibrosis is 25 milligrams per kilogram of subject body weight.

* * * * *